US008512697B2

(12) United States Patent
Fischer et al.

(10) Patent No.: US 8,512,697 B2
(45) Date of Patent: *Aug. 20, 2013

(54) DELIVERY OF MICRO- AND NANOPARTICLES WITH BLOOD PLATELETS

(75) Inventors: Thomas H. Fischer, Hillsborough, NC (US); E. Stan Eskridge, Jr., Chapel Hill, NC (US); Timothy C. Nichols, Chapel Hill, NC (US); Caterina Maria Gallippi, Cary, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 835 days.

This patent is subject to a terminal disclaimer.

(21) Appl. No.: 12/150,562

(22) Filed: Apr. 29, 2008

(65) Prior Publication Data
US 2008/0286366 A1   Nov. 20, 2008

Related U.S. Application Data

(60) Provisional application No. 60/930,364, filed on May 16, 2007.

(51) Int. Cl.
*A01N 63/00* (2006.01)
*A01N 1/02* (2006.01)

(52) U.S. Cl.
USPC ............ 424/93.72; 435/2; 977/830; 977/838

(58) Field of Classification Search
None
See application file for complete search history.

(56) References Cited

U.S. PATENT DOCUMENTS

| 5,427,767 | A  | * | 6/1995  | Kresse et al. ............... 424/9.32 |
| 7,294,455 | B2 | * | 11/2007 | Nichols et al. ............... 435/2   |
| 2003/0082224 | A1 |  | 5/2003  | Noujaim et al. |
| 2005/0025748 | A1 |  | 2/2005  | Nichols et al. |
| 2006/0034809 | A1 |  | 2/2006  | Ho et al. |
| 2006/0240554 | A1 |  | 10/2006 | Chen et al. |
| 2007/0292524 | A1 |  | 12/2007 | Ringe et al. |
| 2008/0020058 | A1 |  | 1/2008  | Chen et al. |

FOREIGN PATENT DOCUMENTS

| JP |  | 8109142 A1 | * | 8/1995 |
| WO | WO 2005/021706 A2 |  |  | 3/2005 |

OTHER PUBLICATIONS

Scull, Christopher M. et al., "Gene Transfer to Macrophages with Nanoparticle-Loaded Platelets", Journal of American Society of Hematology, (ASH Annual Meeting Abstracts) vol. 105, Abstract 3043, 1 Page (2005).
Crawford, N. et al., "Electro-encapsulating drugs within blood platelets: local delivery to injured arteries during angioplasty", Seminars in Interventional Cardiology, vol. 1, No. 1, pp. 91-102 (Mar. 1996).
Koziara, Joanna M., Ph.D., "Nanoparticles as drug carriers across the blood-brain barrier", Thesis, University of Kentucky, 266 Pages (2005).
Lee et al., "Novel Treatment Modalities: New Platelet Preparation and Substitutes", British Journal of Haematology, vol. 114, pp. 496-505 (2001).
Kalambur, Venkatasubramaniam S., "Biotransport of Iron Oxide Magnetic Nanoparticles for Biomedical Applications", Thesis, University of Minnesota, 159 Pages (Jun. 2007).
Johansson, L.O. et al., "A Targeted Contrast Agent for Magnetic Resonance Imaging of Thrombus: Implications of Spatial Resolution", Journal of Magnetic Resonance Imaging, vol. 13, No. 4, pp. 615-618 (2001).
Scull, Christopher M. et al., "Gene Transfer to Macrophages with Nanoparticle-Loaded Platelets", (ASH Annual Meeting Abstracts) [online], vol. 106, No. 11, Abstract 3043, [retrieved on Mar. 15, 2013]. Retrieved from the internet (URL: http://abstracts.hematologylibrary.org/cgi/content/abstract/106/11/3043?max toshow=&hits=80&RESLUTFORMAT=&fulltext= christopher & searchid=1&FIRSTINDEX=0&volume=106& issue=11& resourcetype=HWCIT) (2005).
Al, Hua et al., "Electrostatic Layer-by-Layer Nanoassembly on Biological Microtemplates: Platelets", Biomacromolecules, vol. 3, No. 3, pp. 560-564 (2002).
Cohen, Zoe et al., "Thrombin activity and platelet microparticle formation are increased in type 2 diabetic platelets: a potential correlation with caspase activation", Thrombosis Research, vol. 107, pp. 217-221 (2002).

* cited by examiner

*Primary Examiner* — Robert M Kelly
(74) *Attorney, Agent, or Firm* — Myers Bigel Sibley & Sajovec, P.A.

(57) ABSTRACT

The invention is directed to platelets containing micron or nanometer size particles wherein the micron or nanometer sized particles comprises an active agent. The invention is also directed to a pharmaceutical composition comprising a pharmaceutically acceptable carrier and the above platelets. The invention is further directed to methods of delivering the micron or nanometer size particles containing an active agent to a site of interest in a patient.

14 Claims, 17 Drawing Sheets

Stasix® particles localize to prostate tumors after androgen removal
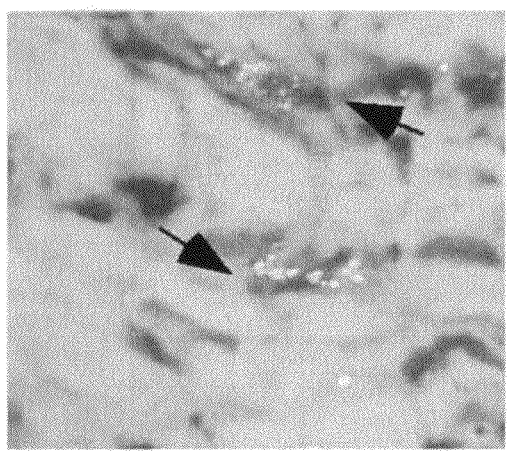 
Two days post androgen withdraw    Pre-androgen withdraw
FIG. 8

Polyethylene Imine/Polyanion – Based Nanoparticles

PEI- <MW> from 3 kDa – 30 kDa for renal clearance $NH_2\text{-}(CH_2CH_2N)_n\text{-}(CH_2CH_2\text{-}NH)_m\text{-}CH_2CH_2\text{-}NH_2$
$|$
$CH_2CH_2\ NH_2$ $\downarrow$ R = -NHS, -lys-protein, -oligo, -DTPA, etc.

polyanion  polycation

5'-UUU UUU Ribavirin-Ribavirin-FITC3'   $NH_2\text{-}(CH_2CH_2N)_n\text{-}(CH_2CH_2\text{-}NH)_m\text{-}CH_2CH_2\text{-}NH_2$
$|$
$CH_2CH_2\ N\diagdown R$ Agglutination reaction PEI-based Nanoparticle Transmission EM of Ribavirin/PEI nanoparticles

FIG. 10

Association of PEI/3'-UUU UUU rbv-rbv-FITC-5' Nanoparticles with Platelets

FIG. 11

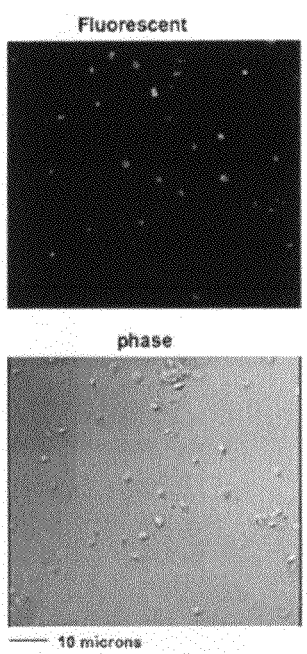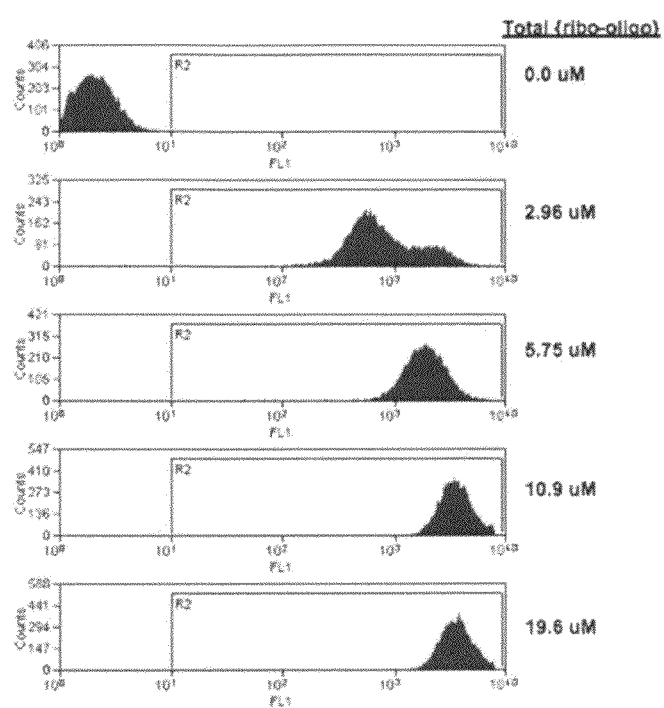
FIG. 14

Monocytes Phagocytize 5'-Biotin-UUU-rbv-rbv-UUU-FITC-3'- BRL Platelets

Fluorescent microscopy of human monocyte
— 10 microns $$\frac{1 \text{ plt/mac} \times 1.1 \times 10^{-17} \text{ moles/plt}}{5.2 \times 10^{-13} \text{ liters/monocyte}} = 2.1 \times 10^{-5} \text{ moles/liter} \quad \text{(vs. IC-50 of 10 uM)}$$

FIG. 15

Small Unilamellar Vesicle – Based Nanoparticles 100 mM octylglucoside
10 mM Phosphatidylcholine
1 mM Phosphatidylethanolamine -$CH_2$N-R
0.01 mM PKH for red fluorescence R = -NHS, -lys-protein, -oligo, -DTPA, etc.

1. Rapid dilution below CMC
2. Residual detergent removed with dialysis

Small Unilamellar Vesicles (SUVs)

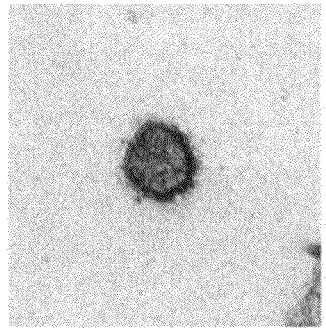

Transmission EM of SUV-based nanoparticle
100 nm

Bilayer structure of SUVs

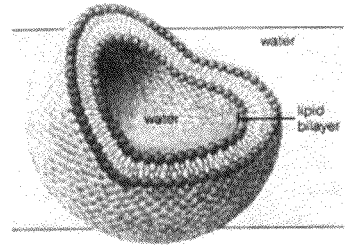

FIG. 16

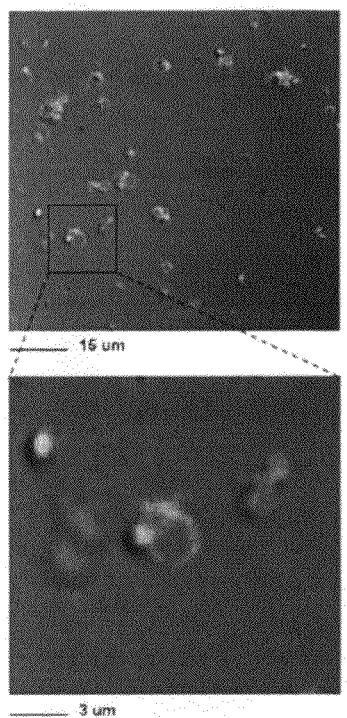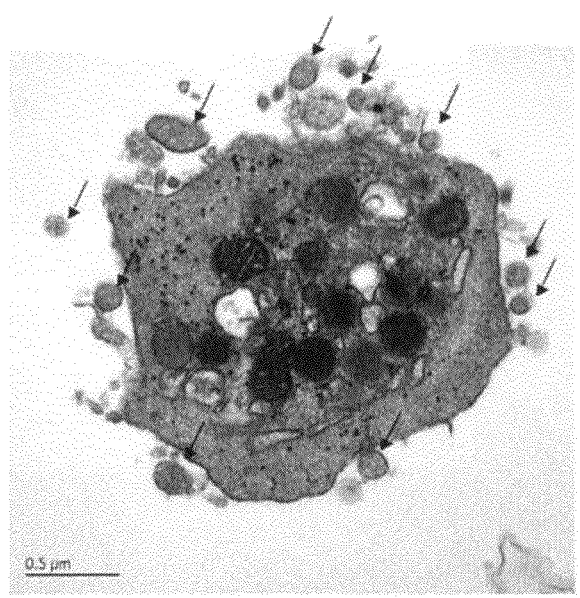
FIG. 17

DELIVERY OF MICRO- AND NANOPARTICLES WITH BLOOD PLATELETS

CROSS-REFERENCE TO RELATED APPLICATIONS

This application claims priority to Provisional Application Ser. No. 60/930,364 filed May 16, 2007.

STATEMENT OF GOVERNMENT SUPPORT

This invention was made in part with government support under grant numbers 5R21EB002863-02 and P20RR020764 from the National Institutes of Health. The government has certain rights in this invention.

BACKGROUND OF THE INVENTION

1. Field of the Invention

The present invention concerns methods and compositions for delivering active pharmaceutical and imaging nanoparticles to a subject in need thereof.

2. Brief Description of the Related Art

Treatment and diagnosis of injuries and infections to vascular tissues is often problematic and the result of difficulties in administering the proper treatment to the site of such injuries or infections. These difficulties have prevented the development of effective treatments for these particular diseases and conditions, examples of which follow. For example, infection with hemorrhagic fever viruses presents a critical challenge to medicine because, among other things, of the severe and frequently fatal consequences of contagion (Borio et. al., JAMA 287, 1-51 (2002)). Hemorrhagic fever is caused by a diverse group of viruses that exert highly varied pathological effects. However, there are two common steps (one early, one late) in the pathogenesis mechanisms of these viruses. First, the preponderance of evidence suggests that infection of macrophages (monocytes), as components of the innate immune system, plays an important initial role in the propagation of the hemorrhagic fever viruses. Secondly, infection by hemorrhagic viruses results in bleeding, and in many instances the wound site is the result of viral damage to vascular cells.

The hemorrhagic fever viruses are members of the Filoviridae, Arenaviridae, Bunyaviridae and Flaviviridae families and have a genome that consists of a single strand of RNA. In general, the viruses work through the following mechanisms: (1) Thrombocytopenia—a reduction in platelet levels is a near-universal consequence of hemorrhagic fever virus infection; (2) Thrombasthenia—The thrombocytopenic condition in hemorrhagic fever can be exacerbated by platelet dysfunctions; (3) Reduced humoral coagulation factor concentrations—decreases in circulating levels of humoral coagulation factors can result from consumption (along with platelets at wound sites or with DIC) and/or damage to hepatic tissue for reduced factor synthesis; and (4) loss of vascular integrity—a loss in endothelial integrity, leading to plasma leakage and the formation of microvascular wound sites, is a common feature in hemorrhagic fever diseases. As a consequence, the pharmaceutical options for treating these viruses is limited.

Ribavirin is a nucleoside analogue that was first reported in 1972 to have broad-spectrum antiviral activities. While ribavirin (monophosphate) has been shown to inhibit inosine monophosphate dehydrogenase for a reduction in cellular GTP, more recent investigations indicate that this nucleoside analogue functions by increasing the intrinsic mutation rate of viruses for "lethal mutagenesis". In tissue culture ribavirin has antiviral activities against a wide variety of viruses, including Flaviviruses, Arenaviruses, and Bunyaviruses. More significantly, ribavirin has been approved by the FDA for the treatment of the Flaviviridae family member hepatitis C virus, and has shown efficacy in the treatment of a limited number of patients with Arenavirus infections.

On the other hand, enthusiasm for ribavirin as an antiviral agent is diminished by three observations. First, promise based on the in vivo performance of ribavirin has not been fully realized in the clinic. For example, ribavirin has been reported to be ineffective in the treatment of infection from members of the Filoviridae and Flaviviridae families (Borio et al., supra). Secondly, this nucleoside analogue has been shown to limit hepatic tissue damage in patients infected with hepatitis C virus, but to require a dual therapy with interferon for viral clearance. Finally, a side effect of ribavirin chemotherapy is the induction of anemia as a result of red blood cell penetration and lyses. Accordingly, there is a need for new ways to administer ribavirin and other such active agents.

Another example is diagnosis of traumatic injuries. An accurate assessment of tissue damage is of paramount importance in the management of traumatic injuries. A key element in this assessment, particularly in patients with unstable or marginally stable hemodynamics, is a determination of the location of sites of internal hemorrhage. Physical examination, traditional X-ray angiography of contrast agents and CT localization of extravascular contrast agent can be used to localize sites of active bleeding. Radiological methods based on labeled red blood cells are useful, but frequently fail to detect bleeding sites. These techniques can be effective, particularly when used together. However, vasospasm and vaso-occlusion, as well as co-localization of several bleeding sites can result in a failure to identify hemorrhage sites. Also, the density of the contrast agent can occlude smaller sites of hemorrhage. This latter problem has been partially ameliorated by using less x-ray dense CO2 contrasting agent. The application of MRI methods developed for detecting vascular defects in hemorrhagic transformation holds promise as tools for localizing wound sites in some types of injuries, including brain trauma and spinal cord injury. However, a fundamental problem with the above methods is that imaging is based on the movement of vascular contents out of the circulatory system, and not directly imaging the actual angiopathic site of vascular breach.

Another example is treatment of cancers, such as prostate cancer. Prostate cancer remains a major cause of morbidity and mortality in middle-aged and older American men. Although several histological types of prostate cancer can be seen following biopsy, the vast majority of prostate cancers are adenocarcinomas of glandular origin. Advarices in diagnosis have resulted in approximately 90 percent of all prostate cancers being found either within the prostate or nearby. For the 90% of cases detected relatively early, the five-year survival rate approaches 100%. In contrast, the 10% representing disseminated disease experiences a five-year survival rate of only 34%. Only skin cancer and the combined mortality of the four common histological types of lung cancer are more common among this population. In 2007, the American Cancer Society anticipates clinical presentation of 218,890 new cases, with primary causation of approximately 27,050 deaths. A remarkable one in six American men will at sometime develop prostate cancer, with one in 34 succumbing to the malignancy.

A brief survey of the potential serious adverse events associated with current standard-of-care therapies illustrates the desirability of less invasive, more carefully targeted, tumor-specific diagnostic and treatment methods. It would be desirable to minimize the damage to healthy prostate, nerve and other extra-prostatic tissues while retaining or enhancing tumor killing efficacy as compared with current standard-of-care surgery or radiation. The serious adverse events which can be associated with prostate cancer surgery (open radical retropubic prostatectomy, open radical perineal prostatectomy, laparoscopic radical prostatectomy or transurethral resection of the prostate) include impotency, incontinence and post-operative infection. The impotency rate after radiation is the same as that of surgery with more than seven out of ten men becoming impotent within five years of having external beam radiation therapy. Although incontinence is less common than after surgery, the risk of incontinence increases every year after radiation until by six years after treatment, the rate is almost as high as that associated with surgery. Androgen ablation remains the standard therapy with advanced prostate cancer and causes disease remission in most men. However, the cancer eventually recurs and thereafter the median survival of patients is less than one year. The results of the proposed program for the development of nanoparticles-loaded platelets for directed energy transfer hold promise for ameliorating many of these difficulties. There is a critical need to improve current standard-of-care in prostate cancer, and the present invention may be an answer to that need.

Another example is treatment of cardiovascular disease and its related vascular pathologies. The unmet nature of the need for therapeutics for cardiovascular disease is evidenced by the expenditures in excess of $300 billion per year for the over 60 million patients in the United States with diagnosed disorders of the cardiovascular system. Most cardiovascular disease is caused by the concerted dysfunction of thrombotic, inflammatory and proliferative processes at sites of vascular injury. For example, acute myocardial infarction is the result of thrombotic occlusion of the coronary circulation that occurs when inflammatory and proliferative processes result in atherosclerotic plaque rupture. Similarly, restenosis after angioplasty and cardiac bypass is the result of initially thrombotic, then inflammatory and proliferative processes at the original vascular injury sites of the procedures. Increased understanding of the molecular mechanisms underlying thrombogenic, inflammatory and atherogenic processes in cardiovascular disease has resulted in numerous strategies for gene therapeutic intervention, including interfering with intracellular signaling and cell cycle control, amplifying anti-thrombotic intracellular signaling, inhibiting pro-atherogenic lipid metabolism. Several methods are currently employed to obtain site-specific gene delivery for cardiovascular gene therapy, including physical targeting with catheter-mediated gene transfer and direct needle injection into adventitia. Additional levels of specificity are obtained by employing tissue-specific promoters (e.g., SM22 for smooth muscle cell delivery). However, further tools for specific delivery of therapeutic compounds to the sites of injuries, including vascular injuries, would be desirable.

Blood platelets are a component of the circulatory and blood systems in the body, and are well-known in the art. U.S. Patent Application Publications 2005/0025748 and 2005/0272161 disclose fixed-dried blood cells and fixed-dried blood platelets that carry an active agent and that are useful to deliver active agents to a site of interest. The blood cells and blood platelets in these applications are "fixed" by chemical treatment with at least one chemical compound that is incorporated into at least a portion of the cells to structurally stabilize and/or extend the shelf-life of the cells. Disclosed fixing agents include formaldehyde, paraformaldehyde and glutaraldehyde, as well as permanganate solutions. However, it would be desirable to eliminate the fixation step in order to more rapidly and cleanly process blood platelets that carry desired agents.

SUMMARY OF THE INVENTION

The invention is a platelet that is loaded with nanoparticles as well as a process for loading the platelets with nanoparticles. The resulted nanoparticle loaded platelets are used to deliver therapeutics and imaging modalities to sites of vascular injury as well as macrophages in human and veterinary medicine. The nanoparticle-loaded platelets can be infused into the systemic circulation or applied topically to injury surfaces.

In one aspect, the invention is directed to platelets containing micron or nanometer size particles, the micron or nanometer sized particles comprising an active agent.

In another aspect, the invention is directed to a pharmaceutical composition comprising a pharmaceutically acceptable carrier and platelets containing micron or nanometer size particles, the micron or nanometer sized particles comprising an active agent, and a pharmaceutically acceptable carrier.

In yet another aspect, the present invention is directed to a method of delivering platelets to a site of interest in a patient, the platelets containing micron or nanometer size particles comprising an active agent, comprising the steps of: providing the above platelets, and administering said platelets to a patient.

These and other aspects will be more fully understood from the following figures and detailed description of the invention.

BRIEF DESCRIPTION OF THE FIGURES

The invention will be more fully understood from the following detailed description taken in conjunction with the accompanying drawings in which:

FIG. 8 shows transmission electron micrographs depicting particles localized to prostate tumors after androgen removal;

FIG. 10 shows preparation of polyethylene Imine/Polyanion-based nanoparticles;

FIG. 11 shows transmission electron micrographs depicting association of labeled nanoparticles with platelets;

FIG. 14 shows platelets loaded with ribavirin;

FIG. 15 shows results of monocytes that phagocytize labeled platelets;

FIG. 16 shows the anatomy of small unilamellar vesicle-based nanoparticles; and

FIG. 17 shows SUV nanoparticles attached to platelets.

DETAILED DESCRIPTION OF THE INVENTION

Figure 1:
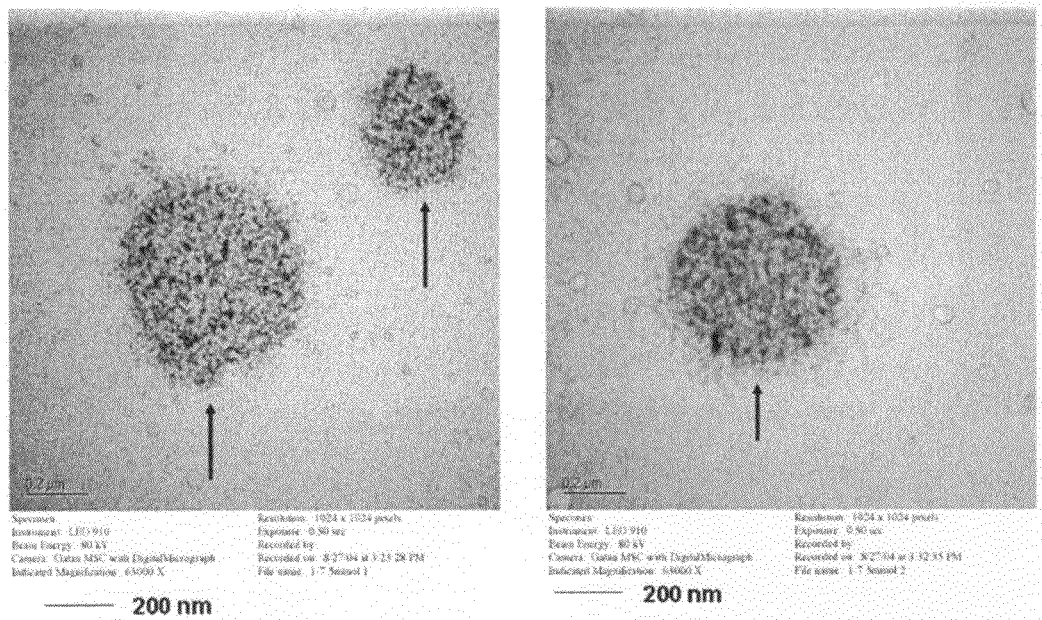
FIG. 1 is a transmission electron micrograph which depicts agglomeration of PEI with plasmid DNA for nanoparticles.

This invention is concerned with the use of platelets as a vehicle to carry various therapeutic or imaging agents. The platelet is a logical vehicle and advantageous for delivering therapeutics to two types of vascular sites for several reasons.

First, it is widely appreciated that platelets bind to sites of vascular breach to provide hemostasis, and it would be advantageous to focus platelets loaded with therapeutics to the site of vascular injury. For example, it would be advantageous if anticancer agents are delivered to tumors where the vasculature is compromised. It would also be advantageous if antiviral agents were delivered to sites of vascular breach in hemorrhagic fevers. In addition, the need to image sites of hemorrhage is important for both diagnostics well as for surgical guidance in traumatic injury.

Secondly, the ultimate fate of platelets that bind to sites of vascular injury is to be phagocytized by macrophages during wound healing processes. Alternatively, the infused cells are removed from the free circulation by macrophages of the reticuloendothelial system (RES). Macrophages are important sites of infection by many types of viruses, including hemorrhagic fever viruses, and are intimately involved with the generation of pathological inflammatory responses. Thus, there are many medical situations where macrophages should be targeted for imaging and anti-inflammatory therapeutic delivery. Macrophage-driven inflammation is frequently the underlying cause of vascular breach, for example in hemorrhagic fever, inflammatory bowel diseases, and hemorrhagic transformation in stroke. The opposite is also true; vascular breach can be the underlying cause of a macrophage-driven inflammatory state. For example, in severe hemorrhagic shock related to excessive blood loss in trauma, a massive systemic release of inflammatory mediators can inactive hemostatic systems, thus exacerbating blood loss. Similarly, macrophage activation is an important driver of multiple organ failure following excessive blood loss. Inflammatory and hematological processes are thus intimately related in a synergistic cause and effect manner. Thus, there are many potential medical applications for platelets that are loaded with therapeutic and imaging nanoparticles.

Subjects to be treated with the methods and compositions of the present invention include both human subjects and animal subjects for veterinary and drug development purposes. Animal subjects are, in general, mammalian subjects, including but not limited to pig, sheep, cow, horse, goat, cat, dog, mouse and rat subjects.

The term "thrombogenic surface" as used herein refers to any natural or artificial thrombogobenic surface, including but not limited to wound tissue, blood vessel plaques such as atherosclerotic plaques, activated endothelium due to local or systemic inflammation, vessels, surfaces or tissues that are rendered thrombogenic in a subject as a toxic side-effect due to administration of anticancer, antineoplastic or antiproliferative agent, surfaces of foreign or implanted items in the subject, including metals, polymers, etc., as found in stents, catheters, biomedical implants such as pacemakers and leads, orthopedic implants such as artificial joints, etc. A compound may be administered to a thrombogenic surface for any purpose, such as for therapeutic purposes or diagnostic purposes (e.g., imaging or detection of a thrombogenic surface by any suitable means such as radioimaging, tissue biopsy, implant removal and determination of whether the delivered compound is found on the implant surface, etc.).

The term "platelets" as defined herein are, in general, of animal, and preferably mammalian, origin (e.g., pig, sheep, cow, horse, goat, cat, dog, mouse, rat, human, etc.). Platelets may be derived from the same species into which the platelets are introduced, or from a different species from which the platelets are introduced. In one embodiment, platelets are harvested from a subject, used to prepare the active agents described herein, and after being so prepared are administered at a later time back to the same subject from which the platelets were harvested. The platelets may be fresh, autologous, allogenic, or rehydrated-lyophilized ("RL").

"Fixed" herein refers to platelets which have been chemically treated with at least one chemical compound that is incorporated into at least a portion of the cells to structurally stabilize and/or extend the shelf-life of the cells. Preferably, the platelets of the present invention are unfixed.

"Fixed-dried" herein refers to platelets which have been fixed, and additionally have had water removed therefrom by any suitable technique such as drying, dehydrating, lyophilizing or freeze-drying, etc., to further structurally stabilize and/or extend the shelf-life thereof.

"Rehydrated" refers to a fixed-dried platelets which have been contacted to or combined with an aqueous solution so that water is taken up into the intracellular space.

"Blood coagulation protein" as used herein includes any suitable blood coagulation protein, including but not limited to Factor VII, Factor IX, Factor X, as well as coagulation proteins that generate Factor VII or FVIIa, such as Factor XII or Factor XIIa, or Factor X or Factor Xa, Protein C, Protein S, and Prothrombin. Such proteins may be natural or synthetic and include proteins containing minor modifications of the naturally occurring protein (i.e., analogs). Where naturally occurring the protein may be of any species of origin, preferably mammalian or human as described herein, and in one embodiment is of the same species of origin as the subject to which it is administered.

"Blood anti-coagulation protein" as used herein includes any suitable blood anti-coagulation protein, including but not limited to activated protein C, protein S, heparin and heparinoids, etc. Such proteins may be natural or synthetic and include proteins containing minor modifications of the naturally occurring protein (i.e., analogs). Where naturally occurring the protein may be of any species of origin, preferably mammalian or human as described herein, and in one embodiment is of the same species of origin as the subject to which it is administered.

"AAV" as used herein refers to "adeno-associated virus".

The term "treat" as used herein refers to any type of treatment that imparts a benefit to a patient afflicted with a disease, including improvement in the condition of the patient (e.g., in one or more symptoms), delay in the progression of the disease, etc.

The term "pharmaceutically acceptable" as used herein means that the compound or composition is suitable for administration to a subject to achieve the treatments described herein, without unduly deleterious side effects in light of the severity of the disease and necessity of the treatment. "Carrier" as used herein means carriers known in the pharmaceutical art that are used in combination with active ingredients to make pharmaceutical compositions. Examples of pharmaceutical carriers include solid, liquid, or aqueous carriers, such as ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride (saline), zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat, and combinations thereof.

The terms "micro" and "nano" when used in reference to particles, refers to sizes of the diameters of the particles. The prefix "micro" refers to particles having diameters larger than 300 nanometers. The prefix "nano" refers to particles having diameters of 300 nm or less.

The micro- and/or nanoparticles of the invention may be made from a variety of materials, including but not limited to natural and synthetic polymers, dendritic networks, aggregates of small molecules, ferromagnetic materials, phospholipid vesicles, micelles, liposomes, and combinations thereof. The micro and/or nanoparticles of the invention may be made using techniques known in the art, including agglomeration as in the case of cationic nanoparticles (see, for example, Lu W, Wan J, She Z, Jiang X. J Control Release. (2007) 118:38-53; Feng M, Lee D, Li P. Int. J. Pharm. (2006) 311:209-214; Gupta K, Ganguli M, Pasha S, Maiti S. Biophys. Chem. (2006) 119:303-306; Dawson M, Krauland E, Wirtz D, Hanes J. Biotechnol. Prog. (2004) 20:851-857; Sennerfors T, Solberg D, Tiberg F. J. Colloid Interface Sci. (2002) 254:222-226), and saturation point precipitation as in the case for iron oxide super paramagnetic nanoparticles (see. for example, Corot C, Robert P, Idee J M, Port M. Adv. Drug Deliv. Rev. (2006) 58:1471-1504; Ma H L, Qi X R, Maitani Y, Nagai T. Int. J. Pharm. (2007) 333:177-186; Thorek D L, Chen A K, Czupryna J, Tsourkas A. Ann. Biomed. Eng. (2006) 34:23-38; Babes L, Denizot B, Tanguy G, Le Jeune J J, Jallet P. J. Colloid Interface Sci. (1999) 212:474-482)

The micro- and/or nanoparticles of the invention may take several forms. In one embodiment, the particles are solid homogeneous particles made from active agent. In another embodiment, these solid particles are coated with an inert material such as polyethyleneimide (PEI) or dextran. Active agents used in the compositions and methods of the invention include therapeutic and imaging agents that include but are not limited to proteins, RNA, DNA, chelation functions, radioactive compounds, ferromagnetic compounds, super-paramagnetic complexes, small molecules, and combinations thereof. Additional examples of active agent include oxygen-filled molecules that become free radicals when irradiated. Malignant tumors frequently have lower oxygen levels than their normal tissue counterparts, and a major mechanism of tumor cell killing by radiation is the formation of cytotoxic free radicals, i.e., chemical species containing a highly reactive free electron.

Further additional examples of active agent include, but are not limited to, nucleic acids such as RNA, DNA, proteins or peptides (enzymes, antibodies, etc,), viruses, bacteria, small organic compounds (e.g., monomers), synthetic and semisynthetic polymers, nanoparticles, chelated metals and ions, etc. Such compounds may have any suitable function or activity depending upon the particular object of the treatment or method, including but not limited to antimicrobial, antibacterial, or antiviral activity; blood coagulation or anti-coagulation activity; reporter or detectable activity, etc. Further additional examples of compounds that may be coupled to platelets to produce active agents of the present invention include, but are not limited to, vasoactive, antioxidant, anti-thrombotic, anticarcinogenic, antiatherogenic, antimitotic, antiangiogenic, and antiproliferative compounds.

In one embodiment of the present invention, the active agent is an antiviral compound. Any suitable antiviral compound can be used, including but not limited to sialic acid analogues, amantadine, rimantadine, zidovudine, vidarabine, idoxuridine, trifluridine, foscarnet, etc. In one embodiment the antiviral compound is a purine nucleoside analog, examples of which include but are not limited to acyclovir, didanosine, ribavirin, ganciclovir, and vidarabine, and antisense nucleosides, RNA and DNA. In one embodiment of the invention, platelets carrying particles loaded with antiviral compounds are administered to patients afflicted with a viral infection in an amount sufficient to treat the viral infection. In one embodiment the patient is infected with a hemorrhagic fever virus, such as a virus of the Filoviridae, Arenaviridae, Bunyaviridae or Flaviviridae families.

The active agent of the particles may also be a drug coagulation protein, such as Factor VII, Factor IX, Factor X, Factor XII, Protein C, Protein S, Prothrombin, anticoagulation proteins such as activated protein C, protein S, heparin and heparinoids, and pro- or anti-coagulation proteins of reptile or insect origin, and others. Such compounds are known. For example, Factor VII or Factor VIa which may be utilized in carrying out the present invention (this term including modified Factor VII or Factor VIIa or Factor VII analogs which retain the blood coagulation activity of Factor VII) is described in, among others, U.S. Pat. Nos. 6,461,610; 6,132,730 6,329,176; 6,183,743; 6,186,789; 5,997,864; 5,861,374; 5,824,639; 5,817,788; 5,788,965; 5,700,914; 5,344,918; and 5,190,919. In one embodiment, recombinant human Factor VIIa is preferred. In another embodiment of the invention, platelets carrying particles loaded with blood coagulation proteins are administered to a subject afflicted with a wound in an amount effective to promote blood coagulation at the wound and/or healing of the wound.

Nucleic acids to be carried in the particles of the invention may encode a detectable protein or peptide such as Lac-Z, beta-glucuronidase, horseradish peroxidase, a fluorescent protein such as green fluorescent protein, etc. In one embodiment of the invention, particles carrying nucleic acids encoding a detectable protein are administered to a subject in an amount effective to express the detectable protein in atherosclerotic tissue or plaques in blood vessels to thereby produce an improved animal model of atherosclerosis. Such animals (which preferably are animals that, by diet and/or breeding are susceptible to atherosclerosis) may be administered a putative antiatherogenic compound, and/or antiatherogenic diet, and then compared to a control animal that has not been administered the putative anti-atherogenic compound and/or anti-atherogenic diet, and the extent of atherogenic plaque formation in experimental animals versus control animals compared by visualizing plaques through expression of the detectable protein. In other embodiments of the invention, the nucleic acid may encode a therapeutic protein or peptide. Examples include, but are not limited to, nucleic acids encoding an anti-atherogenic protein or peptide such as DNA encoding the ras binding domain (RBD) of the ras effector protein $RGL_2$ (e.g., to inhibit proliferation), DNA encoding endothelial nitric oxide synthesize variants (e.g., to inhibit platelet function), DNA encoding the NF-KB super-repressor (e.g., to inhibit inflammatory processes).

The micro- and nanoparticles of the invention may be metallic for a variety of uses, such as echogenic detection. Alternatively, the micro- or nanoparticles may be ferromagnetic, paramagnetic, or super-paramagnetic, such as a super-paramagnetic iron oxide nanoparticle. One example of a super-paramagnetic iron oxide nanoparticle is FERIDEX (ferumoxides injectable solution), available commercially from Bayer. Such ferromagnetic particles may be manipulated with externally applied electromagnetic fields (through mechanisms that include but are not limited to Lorenz forces, magnetostriction, ferromagnetic resonance, and combinations thereof) for the generation of heat (hypothermal therapy) or an acoustic signal. Ferromagnetic particles, such as iron oxide particles, gadolinium particles, magnetite particles, or other known magnetic materials, may also be manipulated to generate heat or an acoustic signal using externally applied electromagnetic fields or magnetic resonance. Such induced physical forces are useful in that they allow for mechanical movement and cellular perturbation of rupturing of the platelet-particle system, as well as induction of coagulation in localized tissue beds. For example, SPIO (super paramagnetic iron oxide) nanoparticles can be subjected to an amplitude-modulated microwave field at the ferromagnetic resonance frequency to generate an acoustic and/or thermal response. This aspect of the invention is particularly useful in vivo imaging for medical diagnostic purposes in humans and animals, particularly if used in conjunction with FDA approved magnetic resonance imaging agents. Polysaccharide covered superparamagnetic oxide colloids, such as disclosed in U.S. Pat. No. 5,262,176, may also be used in the present invention.

Active agent may be incorporated into the micro- or nanoparticles using conventional techniques known in the art, such as coating particles of active agent with a chemical compound. Alternatively, the particles themselves may be a solid sphere of active agent. The platelets are preferably fresh, and may be from any source, such as an individual, or from a stored stock. One useful type of platelet is a lyophilized platelet, or a rehydrated lyophilized (RL) platelet. These platelets may be fixed with a fixative agent such as formaldehyde or paraformaldehyde. One example of a source of rehydrated lyophilized fixed platelets is STASIX (available from Entegrion, Inc., Research Triangle Park, NC). Platelets are loaded with the micro- or nanoparticles of the invention by combining the platelets and particles, and incubating the two for defined periods of time in plasma or selected media, thus allowing the platelets to uptake the micro- and/or nanoparticle through native mechanisms of phagocytosis and/or occlusion that are related to the innate immune function of the platelet. In an alternative embodiment, micro- and/or nanoparticle may be covalently or non-covalently attached to the surface membrane via linkers in native uptake if the nanoparticle does not occur. The platelets are then separated from extracellular (unincorporated) micro- and/or nanoparticle with methods that include but are not limited to differential centrifugation, density gradient centrifugation, size exclusion chromatography, affinity chromatography, elutriation, electrophoresis, and combinations thereof.

According to alternative embodiments of the invention, platelets may be isolated from a subject, loaded with micro- and/or nanoparticle, and then infused back into the subject for therapeutic and/or imaging applications. In another embodiment, loaded platelets may be isolated from a subject, loaded with micro- and/or nanoparticle, and then infused back into another the subject for therapeutic and/or imaging applications. In another embodiment, platelets are normally liquid stored platelets from a single donor or a donor pool, loaded with micro- and/or nanoparticle, and then infused back into one or more subject(s) for therapeutic and/or imaging applications. In another embodiment, the platelets are drawn from a single donor or normally liquid stored platelets from a single donor or a donor pool, loaded with micro- and/or nanoparticle, and then cryopreserved for infusion back into one or more subject(s) for therapeutic and/or imaging applications.

In yet another embodiment, the platelets are drawn from a single donor or normally liquid stored platelets from a single donor or a donor pool, loaded with micro- and/or nanoparticle, and then loaded platelets may be fixed in accordance with known techniques, such as described in U.S. Pat. Nos. 4,287,087; 5,651,966; 5,902,608; 5,891,393; and 5,993,084, frozen and lyophilized. In general, such methods involve contacting said human platelets to a fixative (e.g., an aldehyde) for a time sufficient to fix said platelets; removing said fixative from the platelets; and then drying the platelets to produce fixed-dried blood platelets with loaded micro- and/or nanoparticle. The resulting freeze-dried therapeutic can be rehydrated and then infused back into one or more subject(s) for therapeutic and/or imaging applications. The platelets preferably migrate to a desired site of interest, for example a thrombogenic surface (e.g., wound tissue, blood vessel plaques, sites of inflammation, and the like). Preferably, each platelet contains from about 1 to about 10,000 particles, and more preferably from about 100 to about 1,000 particles.

Recent investigations demonstrate that platelets readily internalize different types of micron and nanometer size particles. These uptake phenomena might be related to the role of platelets in clearing small particulates from the systemic circulation. The incubation of platelets with model viruses results in the internalization of the nanometer-sized pathogens into the blood cell. Similarly, the addition of bacteria to platelet rich plasma results in the apparent internalization of the bacteria[1,2]. The mechanisms through which platelets internalize micron and nanometer size particles are not defined, and the ultimate sites in the platelets to which the particles are transferred are poorly understood. Transmission electron microscopic (TEM) analysis of platelets after an interaction with bacteria indicate that the pathogens are occluded in the surface connected open canalicular system. These have lead to the terming of platelets "covercytes"[1,2]. The possibility exists that, depending on the circumstance, nanoparticles might be transported into internal platelet organelles such as lysosomes, alpha granules or dense granules. These results suggest that platelets play an innate immune role in clearing pathogens from blood, and that these functions can be utilized to direct nanoparticles into this blood cell.

Clues to the mechanisms involved in platelet uptake of nanoparticles can be gleaned from knowledge of how these cells interact with foreign surfaces. The response of platelets to foreign surfaces is hypothesized to occur in three stages: An initial rapid adsorption of plasma proteins, a conformational distortion of the adsorbed plasma proteins, and then functional reaction by platelet surface receptors that is a consequence of the conformational alterations of the adsorbed proteins (see Fischer et al for a review[3]). These events are perhaps best understood for fibrinogen, which behave like a "biosensor" for platelets. Experiments with glass[4] and hydrocarbon polymer-based materials[5-7] show that fibrinogen binds in a distorted conformation, and then interacts with platelet integrins. Current understanding of integrin outside-in signaling processes suggests that integrins bind to domain(s) on the adsorbed fibrinogen molecule that resembles fibrin, and then cluster on the platelet membrane to organize cytoskeletal-related signaling machinery for activation of outside-in signaling[8]. Based on the observation that IgG, fibrinogen and small gold nanoparticles labeled with these proteins are transported to alpha granules[9], it can be hypothesized that some types of nanoparticles that bind IgG and/or fibrinogen might be transferred to alpha granules. Factors that result in the direction of nanoparticles to the surface connected open canalicular system without internalization, as is apparently the case with some pathogens[1,2], are not understood. However, it is logical to speculate that Fc- and complement receptor systems might be involved if nanoparticles are optimized. A more sophisticated understanding of these mechanisms is anticipated to enhance our ability to engineer platelet with internalized imaging and therapeutic nanoparticles.

Nanoparticle-loaded platelets of the present invention can have important medical usage. Upon systemic infusion platelets localize to wound sites where they provide hemostasis and are ultimately are phagocytized by macrophages during wound healing processes. Alternatively, the infused cells are removed from the free circulation by macrophages of the reticuloendothelial system (RES). Thus, the platelets of the present invention can function as carriers (Trojan horses) that can concentrate therapeutics and imaging agents at sites of vascular injury and in macrophages. Other uses and applications of the present invention include medical or veterinary diagnostics, ultrasound, nuclear or infrared imaging, wound or tumor localization, radiation oncology, as well as therapeutic uses, for example, tumor ablation in prostate and breast, and coagulation therapies.

The present invenion overcomes some practical problems with the prior art. While the platelet is the logical vehicle for delivering directed energy transduction agents to destabilized vasculature in prostate tumors, the logistical problem of harvesting and storing platelets renders this application of platelets difficult. In addition to issues of availability and sterility, the current platelet product offered by the blood banking system is functionally unreliable due to storage lesion. A patient's own platelets might be useful for an autologous "arm back to arm" therapy, but secondary health issues related to thrombocytopenia and thrombasthenia in a subpopulation of patients are anticipated to limit this approach. The development of the present invention, as a platelet-based freeze-dried product, removes these limitations.

EXAMPLES

The present invention is further described in detail by means of the following Examples. All parts and percentages are by weight, and all temperatures are degrees Celsius unless explicitly stated otherwise.

Example 1

Uptake of Particles

The ability of platelets to take up sub-micron size particle through native mechanisms is demonstrated here with experiments with polyethyleneimide (PEI) nanoparticles and dextran- coated superparamagnetic iron oxide (SPIO) nanoparticles. PEI-based nanoparticles were prepared by incubating PEI with green-fluorescent protein (GFP) plasmid DNA to obtain a population of approximately round 200-400 nm nanoparticles (FIG. 1).

Figure 2:
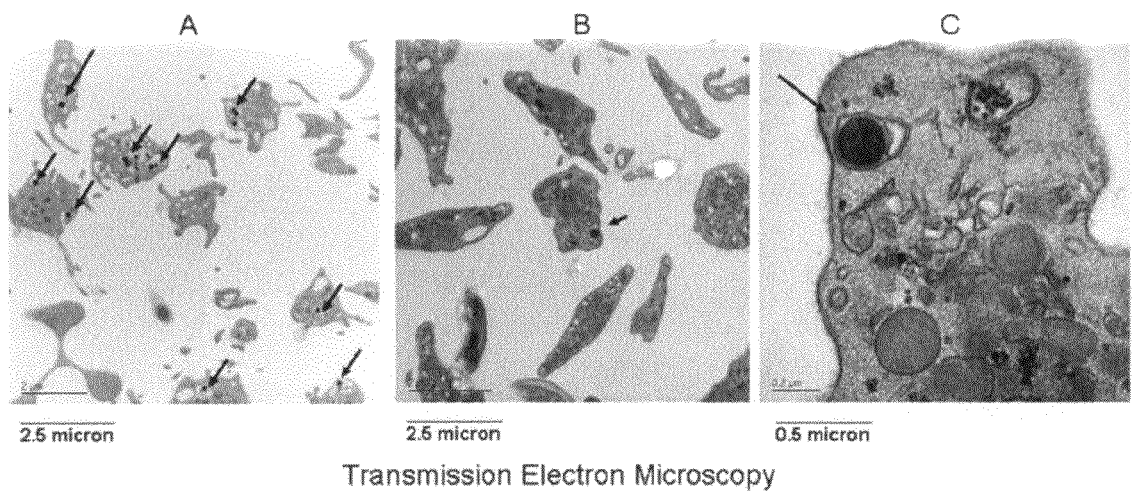
FIG. 2 is a transmission electron micrograph which depicts PEI-Based nanoparticles in platelets.

The resulting nanoparticles were added to freshly prepared human platelet-rich plasma with citrate anticoagulant as described elsewhere [10,11], and allowed to incubate for two hours at room temperature with rocking. The platelets were then removed from excess nanoparticles by centrifuging the cells at 2000×g for ten minutes and then subjecting the platelets to an additional centrifugational wash in citrated saline (3.75 mM citrate, 146 mM NaCl, pH=7.4). The platelets were then subjected to transmission electron microscopy with standard methods[10,11]. This analysis (FIG. 2) showed that most platelets (see Panel A) contained one or more PEI/DNA nanoparticles, and that the nanoparticles were contained (see Panels B and C) in an internal structure with an enclosing bilayer membrane.

Example 2

Internalization of SPIO Nanoparticles

Figure 3:
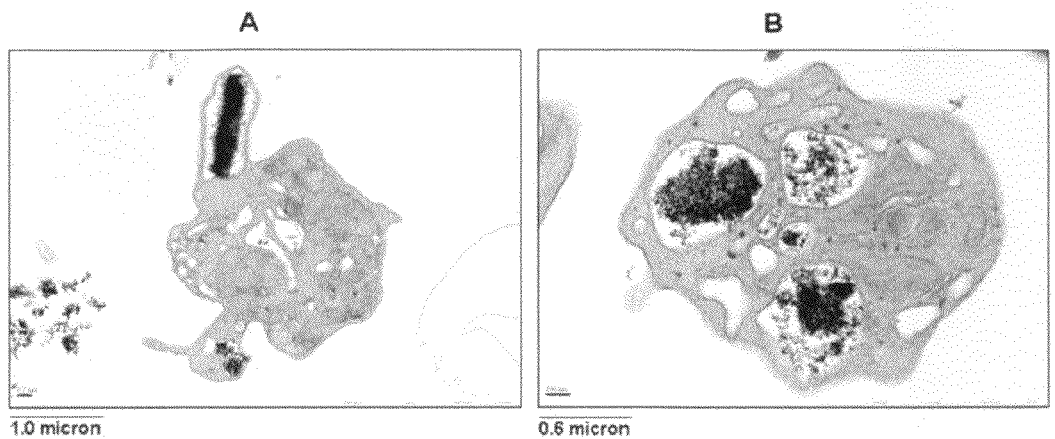
FIG. 3 is a transmission electron micrograph which depicts super-paramagnetic iron oxide nanoparticles in platelets.

The ability of platelets to internalize SPIO nanoparticles was also investigated. Platelets were isolated as described for the studies with PEI nanoparticles, and then incubated with a SPIO-nanoparticle that consists of ~10 nm ferromagnetic iron oxide core coated with dextran (FERIDEX, available commercially from Bayer Healthcare), an infusion-grade product that is approved by the United States Food and Drug Administration for magnetic resonance imaging contrast. The SPIO product was diluted $\frac{1}{10}$ into platelet rich plasma and allowed to incubate with rocking for 12 hours. The mixture was then layered over a density gradient and centrifuged at 2,000×g at room temperature for 10 minutes. The SPIO nanoparticle loaded platelets were collected from the interface, diluted with citrated saline and centrifuged at 2,000×g at room temperature for 10 minutes. The final SPIO platelets were examine with transmission electron microscopy as described for PEI. As was the case for PEI, the SPIO nanoparticles were concentrated in an internal space with a bilayer membrane, likely the surface connected open canalicular system (FIG. 3). The nanoparticles were self-organized into aggregates through magnetic attraction. This example illustrates the utility of the invention in vivo imaging for medical diagnostic purposes in humans and animals.

Example 3

Super-Paramagnetic Platelet Particles for Wound Site Imagine

The goal of these experiments is to deliver the capability to image and provide hemostasis at sites of internal hemorrhage using platelet-based particles that carry super paramagnetic iron oxide (SPIO) nanoparticles for directed energy absorption. Two advances provide the basis for this invention. First, platelets have been found to readily internalize magnetic SPIO nanoparticles (as shown above). Secondly, utilizing the same freeze-drying method that is being used to process platelets as an infusion agent for hemostasis, the SPIO labeled platelets can be freeze-dried to obtain particles loaded with SIPO. The result is a platelet-based product that can in principle be manipulated at internal wound sites with external magnetic fields to generate acoustic and thermal energy. It is the inventors' belief that with the application of external magnetic fields, SPIO loaded particles can be imaged at sites of internal hemorrhage with widely available ultrasound and thermal imaging methods, and can be manipulated to provide hemostasis.

Figure 4:
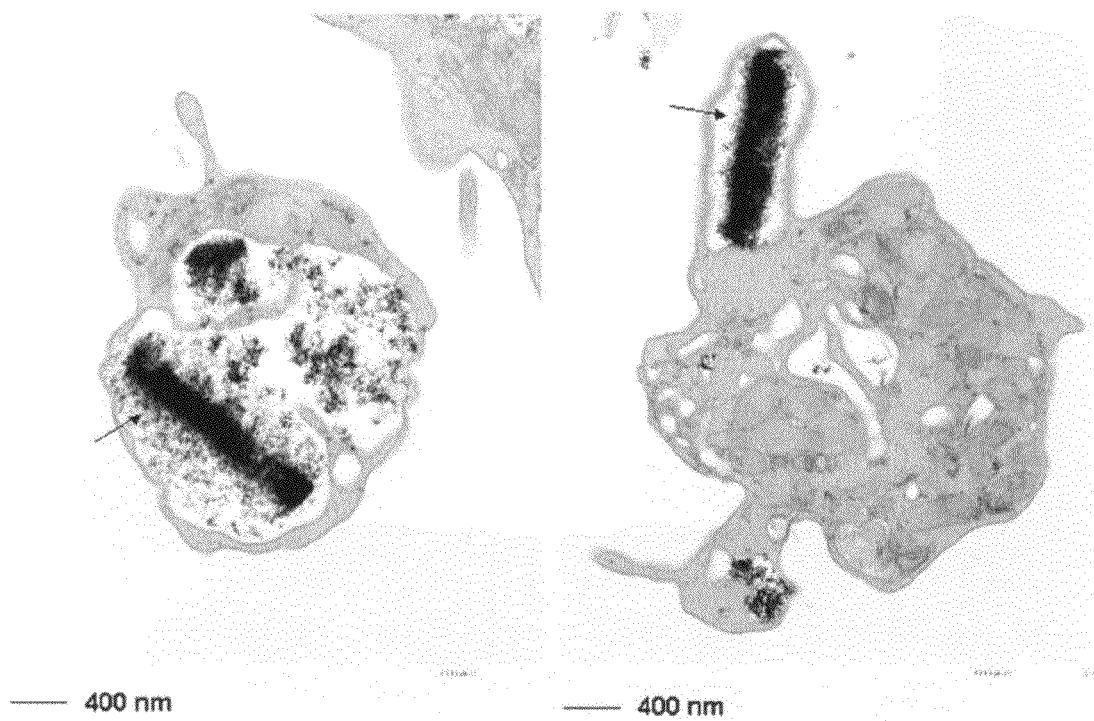
FIG. 4 is a transmission electron micrograph which depicts self organization of SPIO nanoparticles in platelets.

The inventors have discovered that platelets internalize certain types of super-paramagnetic iron oxide nanoparticles in a robust manner. FERIDEX (commercially available from Bayer Healthcare Pharmaceuticals), which consists of ~10 nm super-paramagnetic iron oxide cores with a dextran coating, was incubated with freshly isolated human platelet rich plasma for twelve hours. The platelets were separated from excess contrast agent by layering the mixture on a denisity gradient, centrifuging, and removing the platelets from the media-plasma interface. The Feridex-loaded platelets were then subjected to aldehyde stabilization and lyophilization to obtain a freeze-dried product, referred to here as SPIO-STA- SIX particles. FIG. 4 shows with transmission electron microscopy that the FERIDEX nanoparticles (see arrows) were internalized to form clusters in the surface connected open canalicular system. The SPIO nanoparticles in STASIX particles self-organized to form structures with a rectangular cross-section. These types of structures, which are probably stabilized by nearest neighbor magnetic dipole interactions, are not observed in free suspensions of FERIDEX or in the space between platelets.

Figure 5:
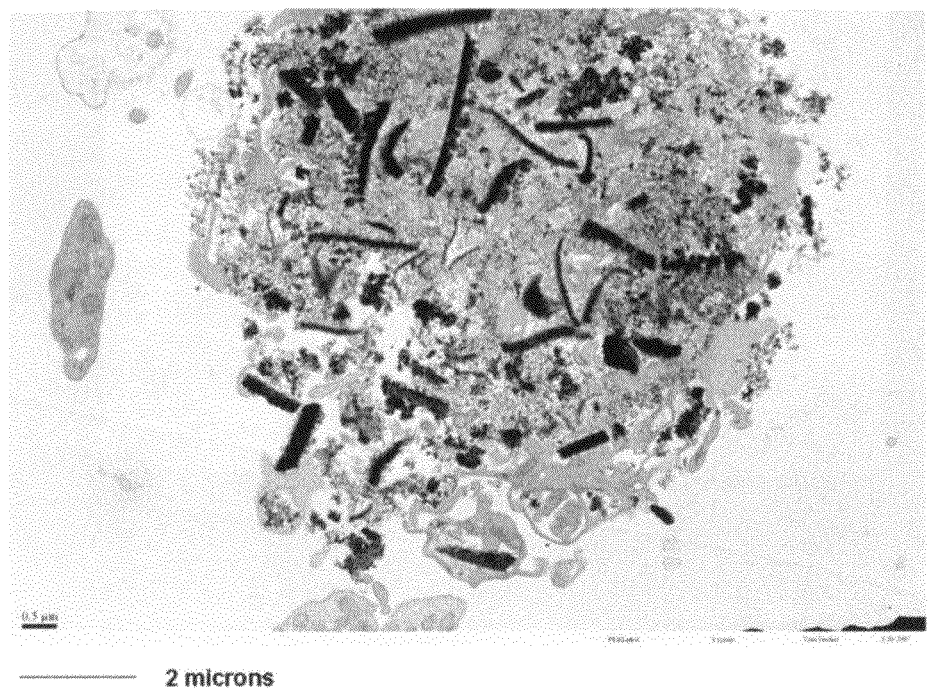
FIG. 5 is a transmission electron micrograph which depicts SPIO loaded particles after modulation by a magnetic field.

Upon exposure to magnetic fields SPIO-STASIX particles were found to undergo a strong activation response for the formation of aggregates. This result is demonstrated in the transmission electron micrograph shown in FIG. 5, where the iron oxide loaded particles in plasma were subjected to a 0.6 Testla field for thirty seconds. The resulting SPIO-STASIX particles were highly aggregated and displayed an activated morphology. This type of observation, which also occurs with 60 Hz osciating magnetic fields (data not shown), provides evidence that SPIO-STASIX particles can be modulated at wound sites to provide hemostasis.

While not wishing to be bound by any particular theory, the observation that platelets can take up iron oxide nanoparticles is not unprecedented. Platelets have been noted to take up several types of particulate materials, including carbon, latex, and cationic ferritin, colloidal gold derivatized with fibrinogen and IgG, model viruses and bacteria are also well-documented. Bacteria are occluded in the surface connected open canalicular system. These observations suggest that platelets play a more important innate immune (host defense) role than is widely appreciated, and that SPIO nanoparticles are accumulated through this set of immunity mechanisms.

Iron oxide nanoparticles have proven safe as an infusion therapeutic in animal and human use. In contrast to many types of nanoparticles that are potentially unsafe due to the presence of toxic components, iron-based nanoparticles have a benign safety profile because of the body's ability to store and transport large quantities of iron. Feridex™ is approved by the United States Food and Drug Administration as an MRI contrast agent for T2 enhancement for the imaging of liver lesions that are associated with the reticulo-endothelial system. When infused into humans, Feridex™ nanoparticles were measurably cleared from blood by the reticulo-endothelial system, then gradually converted to serum iron starting day two. By day seven post administration serum iron levels had returned to normal. These results are consistent with turnover of the canonical iron metabolism cycle.

The physical properties of SPIO lead to the possibility of inducing intrinsic acoustic, thermal and hemostatic responses with applied electromagnetic fields. Because of differences in the velocity of sound in the iron oxide core, SPIO nanoparticles have been found to be echogenic, and are thus detectable with ultrasound. Similarly, because of the magnetic dipole associated with each super-paramagnetic core, SPIO particles can be manipulated with electromagnetic fields. This property underlies the widespread use of the utility of SPIO particles as relaxation contrast agents for MR imaging. SPIO nanoparticles can also be manipulated with radio frequency electromagnetic fields (in the form of radio waves or microwaves) to generate acoustic sound or heat for in vivo hypothermal therapies. Iron oxide is a ferromagnetic material because the spins of unpaired Fe electrons tend to align. In iron oxide particles larger than tens of nanometers spins are aligned in microdomains (Weiss domains); adjacent microdomains are likely to have an antiparallel alignment and the interface of domains (the Bloch wall) is costly from a thermodynamic standpoint. Smaller iron oxide nanoparticles, such as the Feridex™ core, are "super-paramagnetic" because a single domain of aligned unpaired Fe electrons is favored in smaller iron oxide nanoparticles because of the high thermodynamic cost of forming a Bloch wall interface in a small particle. The result of these unique properties is that, in principle, SPIO nanoparticles can be induced to undergo oscillatory mechanical motions with applied electromagnetic fields for the generation of an acoustic signal. The present invention uses interplay between acoustic and electromagnetic field modulation of SPIO in STASIX particles to develop more sensitive imaging modalities.

SPIO nanoparticles can be imaged in prostate malignancies with thermal (induced with near-field RF or microwave), ultrasound (intrinsic or induced resonance) or MRI imaging modalities. In one embodiment, electromagnetic fields, such as radiowaves or microwaves, may be used to modulate the SIPO particles to create an acoustical signal or heat. There are three potential mechanisms through which SPIO nanoparticles can be modulated with electromagnetic fields to produce an acoustic signal. The first mechanism is the Lorentz force. Here, the magnetic component of an applied electromagnetic field can directly couple to the magnetic dipole moment of the SPIO nanoparticle for a force (Lorentz force) that will align and attract the nanoparticle. If the applied electromagnetic field is electromagnetic radiation, then the SPIO particle will be oscillated at the frequency of the radiation, and the nanoparticle will generate an acoustic signal at the frequency of the radiation through a mechanism that is in some ways analogous to how a speaker works. The second method is magnetostriction. Here, an electromagnetic radiation field distorts the material structure (magnetostriction) of the iron oxide nanoparticle in an oscillatory manner, thus generating an acoustic signature. Magnetostrictive effects, which are used on a macroscopic scale in equipment for the generation of ultrasound, are also operant on a microscopic scale with SPIO nanoparticles. The third mechanism is ferromagnetic resonance. Here, microwave (GHz) electromagnetic radiation can drive the unpaired Fe electron spin-spin state transition for ferromagnetic resonance. In contrast to the Lorentz force and magnetostriction effects on nanoparticles, which can be described in classical material mechanical terms, ferromagnetic resonance is essentially a quantum process. Ferromagnetic resonance of magnetic nanoparticles represents a mechanism for strongly coupling an electromagnetic radiation field to mechanical motion for the generation of heat, and ultrasound if the radiation is coherent as generated by a MASOR. Also, if the microwave field at the ferromagnetic resonance frequency is amplitude modulated, the SPIO nanoparticles will generate sound at the modulation frequency. Theoretical aspects of how Lorentz force, magnetostriction and ferromagnetic resonance can result in heat and sound generation from SPIO nanoparticles are well established.

Figure 6:
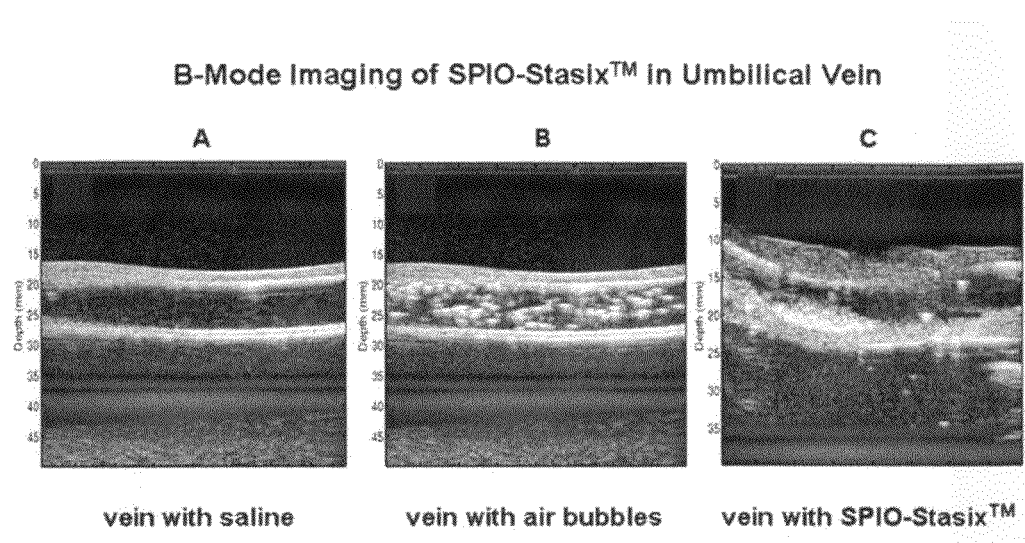
FIG. 6 is a transmission electron micrograph which depicts B-mode imaging of SPIO loaded particles in umbilical vein.

Experiments were performed with SPIO-STASIX particles in a "whole organ" umbilical model to begin to better understand the echogenic properties of platelet-associated SPIO nanoparticles under in vivo conditions. Briefly, an umbilical vein, obtained from a healthy donor undergoing an elective C-section, was tethered into circulation circuit. Sham blood, assembled from packed red blood cells and frozen plasma, was circulated through the circuit while imaging with B-mode ultrasound. A 1.0 ml bolus of 540,00 SPIO STASIX/ µl was infused directly upstream of the umbilical cord while imaging. FIG. 6 depicts the free motion of the SPIO-labeled cells through the uninjured vein. Panels A, B and C respectively depict umbilical veins with saline alone, saline+air bubbles, and saline+a bolus injection of SPIO-STASIX particles (red arrow). The green arrows in panel C are air bubbles.

Figure 7:
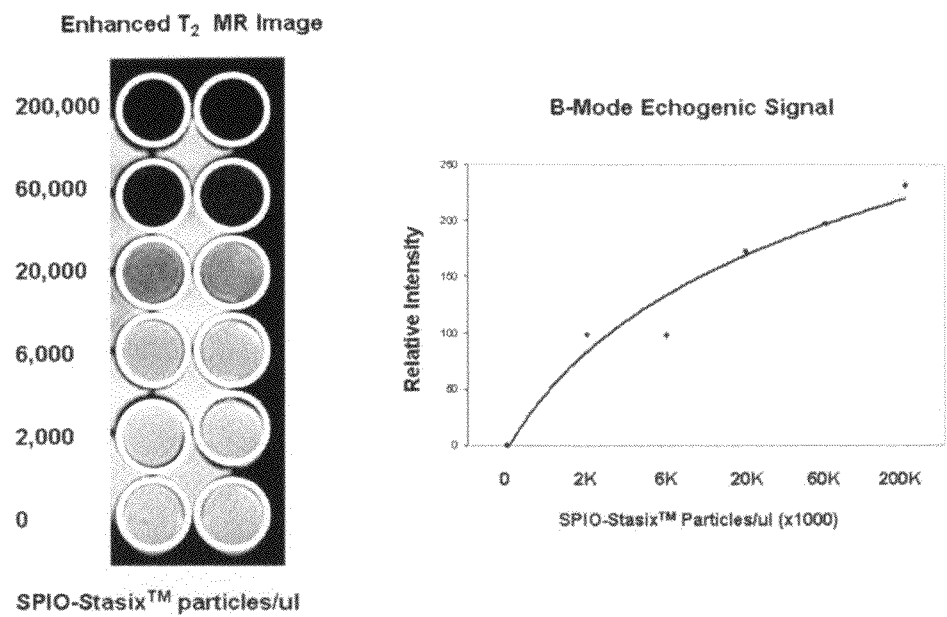
FIG. 7 shows magnetic resonance and echogenic responses of SPIO loaded particles.

Further experiments were performed to determine if SPIO-STASIX particles can be detected with ultrasound as a component of a fibrin clot. SPIO-STASIX was mixed with plasma at different dilutions, and then a clot was formed by adding 1.0 unit/ml thrombin. The preformed clot was then placed on an agarose plate and imaged with magnetic resonance and B-mode ultrasound. FIG. 7 shows that the iron oxide loaded particles can be detected with MR and B-mode ultrasound across physiologically relevant concentration ranges.

Example 4

Anticancer Therapies with Super-paramagnetic Iron Oxide-loaded Particles

The goal of these experiments is to develop improved directed energy transfer methods for imaging, tissue ablation and therapeutic release for the treatment of prostate tumors.

Human prostate tumor resection tissue was implanted on the flanks of immune compromised mice that were supplied superphysiological concentration of androgen. Under these conditions, the xenographic tissue proliferates and the resulting tumors develop a vasculature with an endothelium that is greater than 90% humanoid. Furthermore, the perturbed stellate structure of the endothelial cells that is observed in human prostate tissue is preserved. As is the case with human androgen ablation therapy, withdrawl of the hormone results in massive apoptosis of the endothelium for a wholesale destabilization of the tumor vasculature. Fixed dried platelets were prepared with paraformaldehyde stabilization from fresh human platelets (Read, M. S. et al. Preservation of hemostatic and structural properties of rehydrated lyophilized platelets: potential for long-term storage of dried platelets for transfusion. *Proc Natl Acad Sci USA* 92, 397-401 (1995)), and labeled with a green fluorescent ), and labeled with a green fluorescent CMFDA dye. These fixed-dried platelets are also commercially available from Entegrion, Inc. (Research Triangle Park, NC) under the tradename Stasix. Mice were prepared with human prostate tissue, and then androgen was withdrawn. Bolus doses of $2.0 \times 10^9$ green fluorescent Stasix™ particles/mouse were infused either before or two days after the androgen removal. The animal was sacrificed and then prostate tumor and other tissues were removed and prepared for histological analysis.

Figure 9:
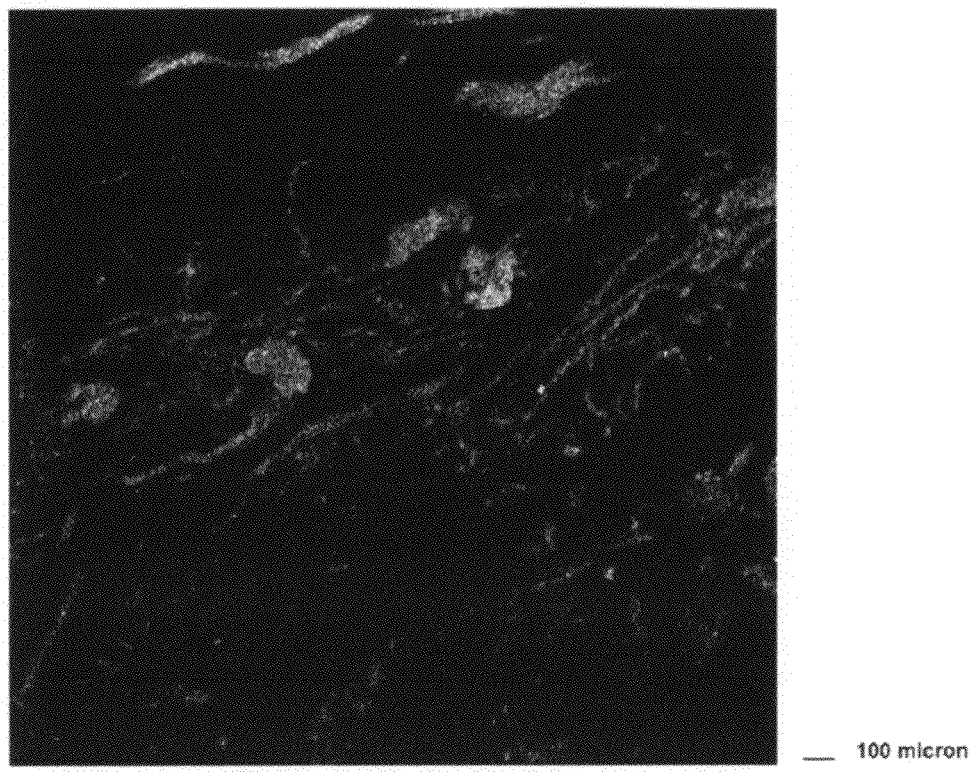
FIG. 9 is a transmission electron micrograph which depicts particles in prostate xenograph tissue.

FIG. 8 depicts the green-fluorescent platelet therapeutic in the tumor vasculature after destabilization (see arrows in left panel). Stasix™ particles were not noted in the tumor tissue before androgen removal (right panel), or in lung, liver or heart tissues (data not shown). FIG. 9 is a 3D reconstruction of confocal images from a prostate tumor after androgen withdraw and green-fluorescent STASIX infusion. The STASIX particles were observed in close proximity to the orange-fluorescent marker for human endothelial cells, essentially co-tracing the tumor vasculature.

Example 5

Preparation of Platelets with Internalized Nanoparticles

Polyethylene imine (PEI), as a polycation, has been extensively utilized to agglutinate cDNA for gene transfection purposes in cell culture and in vivo. The inventors have taken advantage of the ability of PEI to form highly condensed nanoparticulate structures with a wide variety of polyanions ranging in size from small molecules such as ribavirin triphosphate to macromolecules such as cDNA. Two examples of this method, involving the agglomeration of PEI with a rivavirin ribo-oligonucleotide and a DNA plasmid, platelet internalization, and then delivery to macrophages in tissue culture, are presented in the following sections.

(A) PEI-Ribavirin Ribo-Oligonucleotide Nanoparticles Internalization

PEI was condensed with an eight residue rivavirin ribo-oligonucleotide as depicted in FIG. 10. The primary amines of PEI can be labeled under mild conditions with imaging moieties (e.g., fluorophores or MRI agents) and/or functionalities for attachment (e.g., biotin, his6). FIG. 10 depicts a transmission electron micrograph of the 100 nm to 300 nm spherical particles formed when PEI is agglutinated with an eight-mer ribo-oligonucleotide containing two ribavirin residues and a 3'-terminal FITC fluorophore.

Platelets were found to readily internalize PEI-based nanoparticles. The transmission electron micrograph depicted in FIG. 11 shows a PEI/ribavirin ribo-oligomer nanoparticle in the surface connected open canalicular systemAn examination (data not shown) of a large number of platelets at low power demonstrated that virtually all platelets contained one or more PEI nanoparticles. The localization of PEI/anion nanoparticles in the surface connected open canalicullar system is similar to that observed with SPIO nanoparticles, indicating that the innate immune function of platelets is involved in the nanoparticles occlusion event.

(B) Gene Transfer to Macrophages

Figure 12:
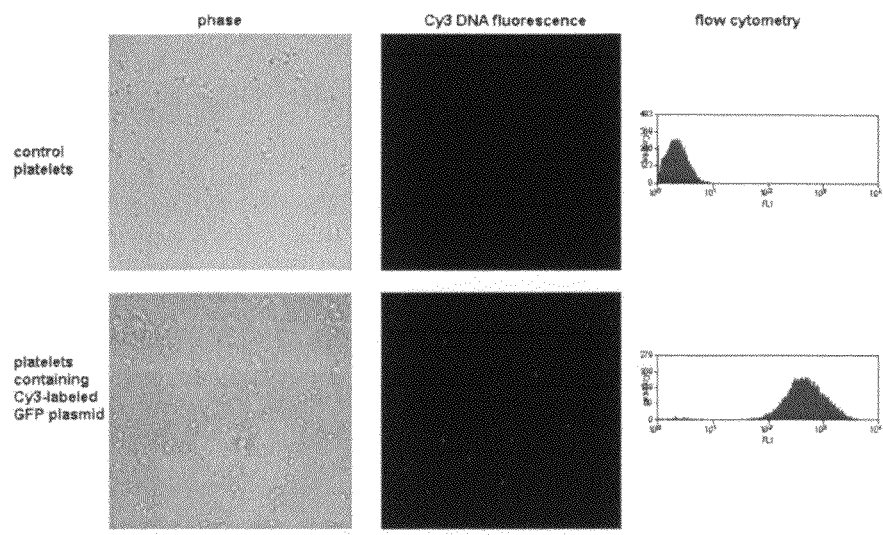
FIG. 12 shows fluorescent microscopic images and flow cytometric profiles of bioengineered platelets.

The following study demonstrates that cDNA-nanoparticle bioengineered platelets can transfer genes to macrophages in tissue culture. In preparation for the gene transfer part of the experiment, green fluorescent protein cDNA was labeled with Cy3 through a linkage that does not interfere with transcription. The red fluorescent cDNA was then condensed with PEI via the method described above to obtain PEI/cDNA nanoparticles. FIG. 12 depicts the fluorescent microscopic image and flow cytometric profile of bioengineered platelets after the cells had internalized the nanoparticles.

Figure 13:
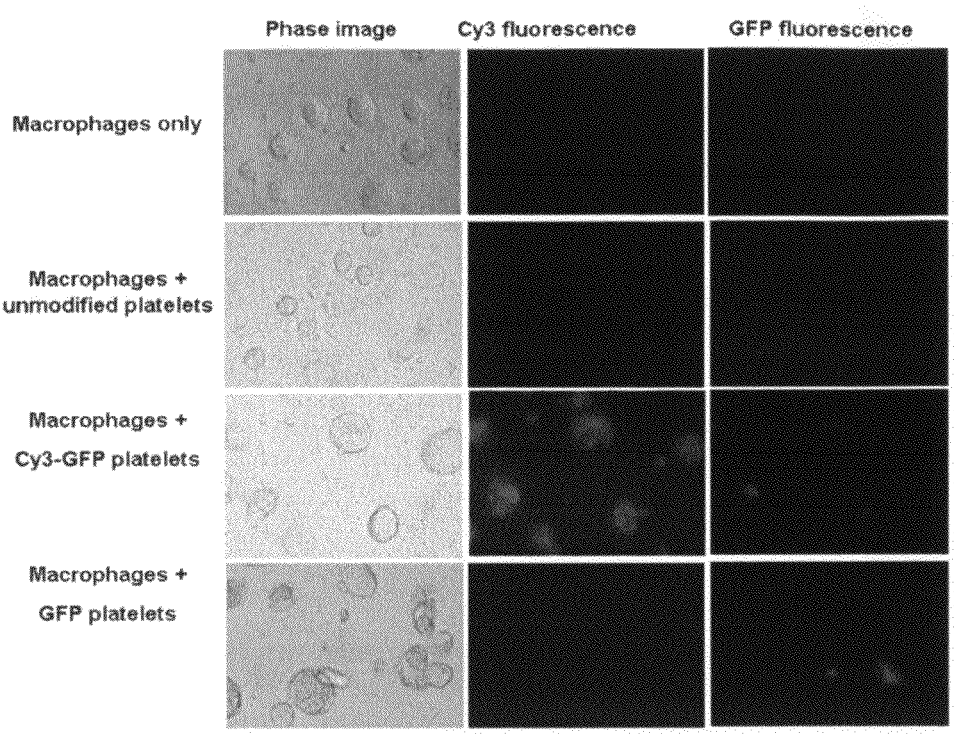
FIG. 13 shows microscopic fluorescence of several platelets.

The gene expression experiment utilized monocytes isolated from peripheral human blood with a density gradient methods. Monocytes were differentiated to macrophages with donor-specific media, and then the innate immune cells were incubated for 12 hours with the GFP-nanoparticle platelets. After an additional 24 hour period the cultures were examined for microscopic fluorescence to determine if the Cy3-labeled cDNA was present in the macrophages (red fluorescence) and if the GFP was expressed (green fluorescence). Appropriate negative controls were performed to demonstrate that macrophage and/or platelet intrinsic fluorescence did not interfere with the experimental analysis. The results are shown in FIG. 13. The principal result of this analysis was that almost all macrophages internalized platelets, and over half expressed the GFP gene.

Example 6

Preparation of Platelets with Surface-Attached Ribavirin

Ribavirin bioengineered Stasix™ particles were prepared in a manner similar to the normal manufacturing process for Stasix™ particles outlined elsewhere. The cells were separated from excess plasma proteins and then subjected to aldehyde stabilization. The surface membranes were then biotinylated with a membrane impermeable NHS biotin analogue. The biotinylated platelets were incubated with excess avidin ([avidin]>>[biotin] and lyophilized. SDS-PAG electrophoresis (along with avidin standards, data not shown) demonstrated that each platelet bound 6.7 million avidin molecules. The avidinated Stasix™ particles were rehydrated and incubated with a ribavirin riboolegonucleotide (5'-biotin'UUU-ribavirin-ribavirin-UUU-FITC-3') that contains two ribavirin bases, a green fluorophore for tracking and a biotin for coupling. The ribooligonucleotide was found to react within seconds to form a tight complex with the avidinated platelets. Fluorescent microscopy (see the FIG. 14) confirmed that the ribavirin probe was attached to the platelets. The flow cytometric titration presented in the right panel of this Figure revealed that the surface-tethered avidin bound the riboolegonucleotide at a molecular ratio of approximately unity for 13.5 million ribavirin moieties per platelet.

The ability of monocytes to internalize the ribavirin-conjugated Stasix™ paricles was tested in a manner analogous to the cDNA nanoparticle macorphage phagocytosis experiment described above. Monocytes were incubated for 12 hours with the ribavirin-conjugated Stasix™ particles, and then examined with confocal microscopy. This analysis (see FIG. 15) shows that the monocytes internalize the platelets. In this Figure, the arrows point to several platelets that have not been internalized. A three-dimensional confocal reconstruction of selected cells (data not shown) revealed that most monocytes had internalized between five and twenty loaded STASIX particles. Based on the internal volume of each monocyte and the number of ribooligonucleotides on each platelet, the internalization of one platelet by a single monocyte results in a local intracellular ribavirin concentration of 21 µMolar. Thus, if several platelets are phagocytized, internal ribavirin concentrations that are well above the IC-50 that has been measured with ribavirin in tissue culture systems are obtained.

Example 7

Surface Tethering of Small Unilamellar Vesicles to Platelets

If therapeutic nanoparticle contents are sensitive to aldehyde fixation, the following type of surface membrane attachment strategy can be used to associate nanoparticles to the platelets after aldehyde fixation and freeze-drying. The practicality of this approach is demonstrated by the following experiment with small unilamellar vesicle (SUVs) nanoparticles. Phospholipid SUVs were formed by rapidly diluting mixed micelles of phospholipids and the detergent octylglucoside (FIG. 16) to final detergent levels below the critical micelle concentration (25 mM for octylglucoside) as detailed elsewhere (Fischer, T. Molecular Crystal Liquid Crystal 102, 141-145 (1984)). For this experiment the bilayers contained a red fluorescent PKH dye for tracking and the primary amine of phosphatidylethanolamine was covalently modified with biotin.

STASIX particles were prepared by the standard manufacturing procedure, with one exception; after the aldehyde fixation step, the exterior side of the surface membrane was covalently modified with an NHS-biotin analogue. The biotinylated STASIX particles were then reacted with a molar excess of avidin to obtain an avidinated membrane. The particles were subjected to SDS-PAG electrophoresis and densiometric scanning (along with lanes with known amounts of avidin) to calculate the number of avidins per platelet; each freeze-dried cell contained~seven million avidins. The biotinylated SUVs were subsequently mixed with the avidinated Stasix™ particles to attach the vesicles to the surface membrane. FIG. 17 depicts the red fluorescent SUVs' association with the surface membrane. The transmission electron micrograph shows the SUVs (indicated by arrows) on the exterior surface membrane. Given the thickness of the TEM section and the discoidal shape of the cell, in this experiment each Stasix™ particle was associated with thirty to sixty SUVs. This experiment demonstrates that nanoparticles can be readily coupled to the surface of bioengineered platelets with biotin-avidin bridge methods.

Example 8

Therapeutic Delivery to Atherosclerotic Plaque

The present invention may be used to deliver therapeutic genes to sites of vascular injury. This ability is shown in FIG. 18. In this study, hypercholesterolemic pigs where placed on a high cholesterol diet for three months to induce atherosclerotic plaque formation. A 1 cm segment of the femoral artery was ligated and then an AAV construct with the Lac Z gene was infused in saline. After one hour the AAV media was removed and the artery was reopened for circulation. One month later the vessel was isolated and histologically analyzed for Lac Z gene product activity. The AAV transduction product was selectively expressed in the atherosclerotic plaque.

Example 9

Prostate Tumor Imaging and Hemostasis with Directed Energy Transfer (A) Preparation of Primary Xenografts of Human Prostate Tissue.

The establishment of primary xenografts of fresh pieces of surgically resected prostate tissue is a routine protocol. Briefly, eight week old immunocompromised mice (SCID or Nu/Nu) are castrated and implanted with a sustained release testosterone pellet 3-7 days before transplantation of the human tissue. Fresh human tissue from radical prostatectomy (prostate cancer) or cystoprostatectomy surgery (benign prostate) are histologically confirmed and received within 2 hours of interruption of the blood supply to the organ during surgery. The prostate tissue is placed immediately in ice cold organ preservation fluid (e.g., ViaSpan™) and transported for transplantation to the prepared immunocompromised host. Eight individual pieces of tissue are implanted subcutaneously on each mouse (four on each flank) and the animals allowed four weeks for the xenografts to establish. Historically, approximately 80% of all freshly transplanted xenografts successfully establish, marked by anastomosis of the human vascular network of the xenograft with the vasculature of the mouse host on the periphery of the xenograft. During the initial fourteen days after transplantation the microvessel density of the human vasculature within the xenografts increases by >5-fold compared to the pre-transplantation tissue. At any time after four weeks, mouse hosts are castrated (the testosterone pellet removed), selectively inducing a wave of apoptosis in the human endothelial cells that peaks on Day 2 post-castration, and has returned to baseline level by Day 5-7 post-castration. It has been determined that the angiogenic response of the prostate xenografts to transplantation and the vascular involution of the human vasculature due to castration occur consistently in all specimens analyzed and are not patient specific responses. Binding of particles to the specifically damaged endothelial layer is compared between the stable vasculature present on Day 0 (no particle localization) and Day 2 (maximal particle localization).

(B) Direct Imaging of Localization

Mouse hosts are infused with low, intermediate and high levels of SPIO-STASIX particles and monitored with B-mode ultrasound and MRI. Animals will be grouped as follows:

| 3,000 | SPIO-STASIX/□l blood vol. | 3 mice on Day 0 and 6 mice on Day 2 |
| 10,000 | SPIO-STASIX/□l blood vol. | 3 mice on Day 0 and 6 mice on Day 2 |
| 30,000 | SPIO-STASIX/□l blood vol. | 3 mice on Day 0 and 6 mice on Day 2 |

Three mice for each treatment group are infused with each concentration of SPIO-STASIX particles on Day 0 before castration, and six mice are infused with each concentration of SPIO-STASIX particles on Day 2 post-castration. The animals will be infused with the particles, the platelets allowed to circulate for forty-five minutes, and the animal imaged. Subsequent to imaging, the animal is euthanized, the xenografts harvested and prepared for histologic analysis and for quantification of the amount of iron within the xenograft/wet weight tissue.

Animals are monitored with ultrasound in B-mode and with acoustic radiation force impulse (ARFI) pulse sequences. Mice are then be subjected to MR imaging with two registered imaging sequences designed to provide both registered anatomic landmarks and improved sensitivity to the presence of iron nanoparticles. A 3D diffusion weighted projection encoded image will be acquired with an anisotropic image array of 512×512×64. A variation of the same sequence designed to provide improved sensitivity to local field inhomogeneities (T2* sensitive) may be used to detect the nanoparticles. At the conclusion of the in vivo studies, MR histology of xenografts can be performed to provide higher spatial resolution 3D image sets for more complete quantification of the extent of tumor geometry and the localization of nanoparticles. The work on perfusion fixed specimens (fixed in situ) can be performed at 9.4T using the above described 3D encoding methods that have been described previously and which are known in the art. After MR histology host animals are sacrificed; xenografts harvested, fixed, embedded and sectioned; and fluorescent and transmission electron microscopic examinations performed.

(C). Directed Energy Transfer

Animals are positioned between an infrared camera and the electromagnetic near field source, with an ultrasound transducer in direct contact with animal's skin. Before, and at 45 minutes after the SPIO-STASIX particle infusion, a radiofrequency is applied for the generation of thermal and/or acoustic responses via Lorentz force-mediated mechanisms. This experiment also may be performed with the application of a microwave field for induction of ferromagnetic resonance. Animals are monitored for induced thermal and acoustic signals. Groups of six animals are evaluated at low, intermediate and high SPIO-STASIX particle concentrations, as follows.

|  | Intrinsic | RF nearfield | Microwave |
| --- | --- | --- | --- |
| Thermal | ~ | 3 mice | 3 mice |
| Ultrasound | 3 mice | 3 mice | 3 mice |
| MRI | 3 mice | ~ | ~ |

After monitoring the acoustic and thermal signals, animals are sacrificed and subjected to a histological evaluation as detailed in the last section to verify SPIO-STASIX particle distribution and localization.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entireties.

REFERENCES

1. White J G. Why human platelets fail to kill bacteria. Platelets. 2006; 17:191-200
2. White J G. Platelets are covercytes, not phagocytes: uptake of bacteria involves channels of the open canalicular system. Platelets. 2005;16:121-131
3. Fischer T, Smith C J, Vournakis J N. Mechanisms for the interaction of foreign materials with hemostatic systems. In: Columbus F, ed. New Research on Biomaterials. Hauppauge, N.Y.: Nova Science Publishers, Inc.; 2006
4. Coller B S, Peerschke E I, Scudder L E, Sullivan C A. A murine monoclonal antibody that completely blocks the binding of fibrinogen to platelets produces a thrombasthenic-like state in normal platelets and binds to glycoproteins IIb and/or IIIa. J Clin Invest. 1983;72:325-338
5. Goodman S L, Cooper S L, Albrecht R M. Integrin receptors and platelet adhesion to synthetic surfaces. J Biomed Mater Res. 1993;27:683-695
6. De Scheerder I, Verbeken E, Van Humbeeck J. Metallic surface modification. Semin Interv Cardiol. 1998;3:139-144
7. Nagai H, Handa M, Kawai Y, Watanabe K, Ikeda Y. Evidence that plasma fibrinogen and platelet membrane GPIIb-IIIa are involved in the adhesion of platelets to an artificial surface exposed to plasma. Thromb Res. 1993;71: 467-477
8. Juliano R L. Signal transduction by cell adhesion receptors and the cytoskeleton: functions of integrins, cadherins, selectins, and immunoglobulin-superfamily members. Annu Rev Pharmacol Toxicol. 2002;42:283-323
9. Escolar G, White J G. The platelet open canalicular system: a final common pathway. Blood Cells. 1991;17:467-485; discussion 486-495
10. Fischer T H, Merricks E P, Bode A P, Bellinger D A, Russell K, Reddick R, Sanders W E, Nichols T C, Read M S. Thrombus formation with rehydrated, lyophilized platelets. Hematology. 2002;7:359-369
11. Fischer T, Bode, A P, Parker, B P, Russell, K E., Bender, D E, Ramer, J K and Read, M S. Primary and secondary hemostatic functionalities of rehydrated, lyophilized platelets. Transfusion. 2006; in press

What is claimed is:

1. Platelets containing super-paramagnetic iron oxide nanoparticles.

2. The platelets of claim 1, wherein said platelets comprise mammalian blood platelets.

3. The platelets of claim 1, wherein said platelets comprise human blood platelets.

4. A pharmaceutical composition comprising a pharmaceutically acceptable carrier and platelets containing super-paramagnetic iron oxide nanoparticles.

5. The pharmaceutical composition of claim 4, wherein said platelets comprise mammalian blood platelets.

6. The pharmaceutical composition of claim 4, wherein said platelets comprise human blood platelets.

7. The pharmaceutical composition of claim 4, wherein said carrier is a sterile carrier.

8. The pharmaceutical composition of claim 4, wherein said carrier is a solid carrier.

9. The pharmaceutical composition of claim 4, wherein said carrier is a liquid carrier.

10. The pharmaceutical composition of claim 4, wherein said carrier is an aqueous carrier.

11. The platelets of claim 1, wherein said platelets are fresh.

12. The platelets of claim 1, wherein said platelets are rehydrated-lyophilized.

13. The pharmaceutical composition of claim 4, wherein said platelets are fresh.

14. The pharmaceutical composition of claim 4, wherein said platelets are rehydrated-lyophilized.

* * * * *

UNITED STATES PATENT AND TRADEMARK OFFICE
CERTIFICATE OF CORRECTION

PATENT NO. : 8,512,697 B2  
APPLICATION NO. : 12/150562  
DATED : August 20, 2013  
INVENTOR(S) : Fischer et al.

It is certified that error appears in the above-identified patent and that said Letters Patent is hereby corrected as shown below:

In the Specification

Column 1, STATEMENT OF GOVERNMENT SUPPORT, Lines 13-16: Please correct the entire government support statement to read as follows:

-- This invention was made with government support under Grant numbers RR020764, HD001441, and EB002863 awarded by the National Institutes of Health. The government has certain rights in the invention. --

Signed and Sealed this  
Twenty-fourth Day of March, 2015

Michelle K. Lee  
*Director of the United States Patent and Trademark Office*